United States Patent [19]
Griffiths et al.

[11] Patent Number: 6,156,510
[45] Date of Patent: Dec. 5, 2000

[54] POLYMORPHISMS IN A MICROSATELLITE REGION OF A GLUCOCORTICOID RECEPTOR GENE

[75] Inventors: Lynette Robyn Griffiths, Burleigh Heads; Susan Rutherford, Brisbane; Brian James Morris, Sydney, all of Australia

[73] Assignee: Gemini International Holdings Limited, Monaco

[21] Appl. No.: 08/982,293

[22] Filed: Dec. 2, 1997

[51] Int. Cl.[7] .............................. C12Q 1/68; C12P 19/34; C07H 21/04

[52] U.S. Cl. ........................... 435/6; 435/91.2; 536/23.1; 536/24.1; 536/24.31; 536/24.33

[58] Field of Search ..................... 435/6, 91.2; 536/23.1, 536/24.33, 24.31, 24.1

[56] References Cited

U.S. PATENT DOCUMENTS

| | | | |
|---|---|---|---|
| 5,405,872 | 4/1995 | McDermed et al. | 514/605 |
| 5,409,936 | 4/1995 | Honma et al. | 514/303 |
| 5,496,569 | 3/1996 | Morris, Jr. et al. | 424/717 |
| 5,510,390 | 4/1996 | Bergeron, Jr. | 514/673 |
| 5,582,979 | 12/1996 | Weber | 435/6 |

OTHER PUBLICATIONS

Heeley et al. Biochemical Society Transactions. Meeting Dec. 10–13, 1996. 25:236S Laghi et al. Gastroenterology. 112:A598, May 1997.

Laghi et al. Proceedings of the American Association for Cancer Research. 38:520, abstract #3489, Mar. 1997.

Karl, M. et al., "Familial Glucocorticoid Resistance Caused by a Splice Site Deletion in the Human Glucocorticoid Receptor Gene," *J. Clin. Endocrinol. Metab.* 76:683–689 (1993).

Li, X. et al., "A YAC Contig of Approximately 3 Mb from Human Chromosome 5q31→q33," *Genomics* 19:470–477 (1994).

Weber, J.L. et al., "Mapping of Human Chromosome 5 Microsatellite DNA Polymorphisms," *Genomics* 11:695–700 (1991).

Ying, L. –H. et al., "Association of RFLP for the Insulin Receptor Gene, but not Insulin, with Essential Hypertension," *Biochem. Biophys. Res. Commun.* 181:486–492 (1991).

Zee, R.Y.L. et al., "Association of *Hinc*II RFLP of Low density lipoprotein receptor gene with obesity in essential hypertensives," *Clin. Genet.* 47:118–121 (1995).

Caterson, I.D., "Obesity, Part of the Metabolic Syndrome," *Clin. Biochem. Revs.* 18:11–21 (Feb. 1997).

Jabs, E.W. et al., "Genetic and Physical Mapping of the Treacher Collins Syndrome Locus with Respect to *Loci* in the Chromosome 5q3 Region," *Genomics* 18:7–13 (1993).

Jeunemaitre, X. et al., "Molecular Basis of Human Hypertension: Role of Angiotensinogen," *Cell* 71:169–180 (1992).

Takami et al. Journal of Applied Physiology. 276:H1379–H1384, Apr. 1999.

Lin et al. Hypertension. 34:1186–1192, Dec. 1999.

Brand et al. Hypertension. 33:1175–1178, 1999.

Kato et al. Hypertension. 32:935–938, 1998.

*Primary Examiner*—Carla J. Myers
*Attorney, Agent, or Firm*—Sterne, Kessler, Goldstein & Fox P.L.L.C.

[57] ABSTRACT

A method of diagnosis of a disease, Syndrome X in one embodiment, in an individual comprises determining the genotype of a microsatellite region of a glucocorticoid receptor gene in said individual. A method of identifying an individual predisposed or susceptible to the disease comprises determining the genotype of a microsatellite region of a glucocorticoid receptor gene in said individual. Methods of treatment and therapy for diseased or predisposed or susceptible individuals are provided, together with apparatus for carrying out the diagnosis.

15 Claims, No Drawings

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: both (ii) MOLECULE TYPE: cDNA (xi) SEQUENCE DESCRIPTION: SEQ ID NO:1:

TTGGAAGCCT TAGGAAGTGC        20

(2) INFORMATION FOR SEQ ID NO:2:

(i) SEQUENCE CHARACTERISTICS:
      (A) LENGTH: 22 base pairs
      (B) TYPE: nucleic acid
      (C) STRANDEDNESS: single
      (D) TOPOLOGY: both (ii) MOLECULE TYPE: cDNA (xi) SEQUENCE DESCRIPTION: SEQ ID NO:2:

AAGAATTCTA GTTTCAATAC CG        22

POLYMORPHISMS IN A MICROSATELLITE REGION OF A GLUCOCORTICOID RECEPTOR GENE

FIELD OF THE INVENTION

This invention relates to polymorphism in a microsatellite region of a glucocorticoid receptor gene and to diagnostic method and apparatus based upon the polymorphism, in particular a polymorphism near the 3' end of the glucocorticoid receptor gene. The invention also relates to methods of identifying individuals having a predisposition or susceptibility to Syndrome X and to methods of treating those individuals to prevent, delay or reduce disease.

BACKGROUND OF THE INVENTION

Essential hypertension or sustained high blood pressure is a genetic disorder that affects 20% of the Caucasian population and predisposes individuals to other disorders such as stroke, and renal and cardiovascular disease. Hypertension is also known to cluster with obesity and other disorders such as non-insulin dependent diabetes (NIDDM), atherosclerosis, vascular disease and dyslipidaemia in a metabolic syndrome known as Syndrome X. Identifying the cause of hypertension and Syndrome X susceptibility has been hindered by the complex genetics of the disorder and its interaction with environmental triggers. Candidate gene approaches offer a method to identify genes involved and have been used successfully to identify two genes involved in the disorder (Jeunemaitre X, Soubrier F, Kotelevtsev Y V, Lifton R P, Williams C S, Charru A, Hunt S C, Hopkins P N, Williams R R, Lalouel J, Corvol P. Molecular Basis of Human Hypertension: Role of Angiotensinogen. Cell 1992; 71: 169–180, and Ying L, Zee R Y L, Griffiths L R, Morris B J. Association of a RFLP for the insulin receptor gene, but not insulin, with essential hypertension. Biochem Biophys Res Comm 1991; 181: 486–492).

Results from these studies may lead to better targeted treatments. If the genes that cause susceptibility to Syndrome X disorders can. be identified, then treatments for specific gene defects can be targeted. At present such targeted treatment strategies are not available, but once diagnostic tests for disease susceptibility in these fields are developed such treatments will become available. At present, the only available treatments for these disorders are pharmaceutical based medications that are not targeted to an individual's actual defect; examples include ACE inhibitors and diuretics for hypertension, insulin supplementation for NIDDM, cholesterol reduction strategies for dyslipidaemia, anti-coagulants, β blockers for cardiovascular disorders and weight reduction strategies for obesity.

However, no gene approaches have to date provided for diagnosis of predisposition or susceptibility to hypertension or other components of Syndrome X to enable treatment before the symptoms and effects of disease become established.

SUMMARY OF THE INVENTION

It is an object of the invention to provide genetic diagnosis of predisposition or susceptibility to Syndrome X, and to hypertension in particular. Another related object is to provide treatment to reduce or prevent or delay the onset of disease in those predisposed or susceptible to this disease. A further object is to provide means for carrying out this diagnosis.

The function of the glucocorticoid receptor is to mediate the behavioural, cardiovascular, inflammatory and metabolising actions of glucocorticoids—steroid hormones that are regulated by corticotrophin (ACTH) and partly by the level of glucocorticoids themselves in the blood stream. Karl et al (Karl M, Lamberts S W, Detera-Wadleigh S D, Enclo I J, Stratakis C A, Hurley D M, Accili D, Chrousos G. P. Familial glucocorticoid resistance caused by a splice site deletion in the human glucocorticoid receptor gene. J Clin Endocrinol Metab 1993; 76: 683–689) have reported glucocorticold resistance occurring from a splice site deletion in the region of the gene coding for the ligand binding domain of the receptor.

The present invention stems from our testing of a microsatellite region proximal to a glucocorticoid receptor gene, in particular a microsatellite marker, D5S207 (Weber J, Polymeropoulos M H, May P E, Dwitek A E, Xiao H, McPherson J O, Wasmuth J J. Mapping of Human Chromosome 5 Microsatellite DNA Polymorphisms. Genomics 1991; 11: 695–700), located within a 200 kb YAC containing the glucocorticoid receptor gene (Li X, Wise C A, Paslier D L, Hawkins A L, Griffin C A, Pittler S J, Lovett M, Jabs E W. A. YAC contig of Approximately 3 MB from Human Chromosome 5q31- q 33. Genomics 1994; 19:470–477) in a case control cross-sectional hypertension study. Consequently, references in the present invention to a microsatellite region of the glucocorticoid receptor gene are intended to be references to a region consisting of the microsatellite marker D5S207 plus DNA within 2000 kb of the 5' end of the marker and DNA within 2000 kb of the 3' end of the marker. This region thus includes the microsatellites 3' to the glucocorticoid receptor gene.

DESCRIPTION OF THE PREFERRED EMBODIMENTS

Accordingly, a first aspect of the invention provides a method of diagnosis of disease in an individual, said method comprising determining the genotype of a microsatellite region of a glucocorticoid receptor gene in said individual.

In another aspect, the invention provides a method of identifying an individual predisposed or susceptible to a disease, said method comprising determining the genotype of a microsatellite region of a glucocorticoid receptor gene in said individual.

The invention is of advantage in that it enables diagnosis of a disease or of certain disease states via genetic analysis which can yield useable results before onset of disease symptoms, or before onset of severe symptoms. The invention is further of advantage in that it enables diagnosis of predisposition or susceptibility to a disease or of certain disease states via genetic analysis.

The invention may also be of use in confirming or corroborating the results of other diagnostic methods. The diagnosis of the invention may thus suitably be used either as an isolated technique or in combination with other methods and apparatus for diagnosis, in which latter case the invention provides a further test on which a diagnosis may be assessed.

Certain disease states would benefit, that is to say the suffering of the patient may be reduced or prevented or delayed, by administration of treatment or therapy in advance of disease appearance; this can be more reliably carried out if advance diagnosis of predisposition or susceptibility to disease can be diagnosed.

In a particular embodiment of the invention, the method comprises determining genotype of a microsatellite located 3' to the coding sequence of the glucocorticoid receptor gene. The microsatellite is preferably selected from the group consisting of D5S207, D5S210, D5S376, CSFLR, SPARC, D5S119, D5S209 and FGFR4.

The method of the invention optionally comprises determining whether an individual is homozygous or heterozygous for polymorphisms of said glucocorticoid receptor gene. A determination that an individual is free of a risk genotype may provide a more significant diagnosis. Likewise, the presence of two risk alleles may give a significant diagnosis of predisposition to disease.

In an embodiment of the invention, the disease is Syndrome X. The invention thus assists in identifying those individuals predisposed or susceptible to this syndrome, enabling early commencement of therapy or treatment or other techniques to avoid or reduce the disease, these latter including adopting a different lifestyle or a different diet. A number of individual disorders are known to be contained within or typically contribute to or feature in Syndrome X and references to Syndrome X are intended to be references to one or more diseases selected from the group consisting of hypertension, obesity, non-insulin dependent diabetes, atherosclerosis, vascular disease and dyslipidaemia.

It is therefore a further aspect of the invention to provide a method of treatment of an individual comprising determining genotype of a microsatellite region of a glucocorticoid receptor, determining if that individual is predisposed or susceptible to Syndrome X, and if that individual is so diagnosed providing treatment to reduce or delay or prevent disease.

Current treatments and therapies for Syndrome X are all of application in the present invention for treatment and therapy for an individual diagnosed as predisposed or susceptible to Syndrome X. Insulin supplements are suitable for non-insulin dependent diabetes. A strategy to reduce cholesterol intake is suitable for dyslipidaemia. Anti-coagulants and 8-blockers are suitable for cardiovascular disorders. Weight reduction strategy is suitable for obesity.

In a specific embodiment of the invention there is provided diagnosis of predisposition or susceptibility to hypertension Suitable hypertension treatments are disclosed in U.S. Pat. Nos. 5,510,390, 5,496,569, 5,405,872 and 5,409,936, the contents of which are incorporated herein by reference. Accordingly, the method may further comprise a treatment selected from the group consisting of administration of an effective amount of antihypertensive pharmaceutical, administration of an effective anti-hypertension therapy or administration of both an effective anti-hypertension therapy and an effective amount of anti-hypertensive pharmaceutical.

Anti-hypertension therapy may include correction of obesity, high alcohol intake, high salt intake and/or lack of regular exercise. Anti-hypertensive pharmaceutical may include beta-adrenoceptor blocking drugs, optionally in combination with a thiazide, calcium channel blockers, acetylcholinesterase inhibitors, vasodilators, alpha-blockers, acetylcholinesterase (ACE) inhibitors and centrally acting drugs such as prazosin, terazosin and doxazosin.

Determination of the genotype of said microsatellite region of a glucocorticoid receptor gene is suitably accomplished by screening the 3' region of said glucocorticold receptor gene to identify a polymorphism near said 3' region of said glucocorticoid receptor gene, said polymorphism being indicative of a risk genotype in said individual. In an embodiment of the invention, the screening is accomplished by a technique selected from the group of techniques consisting of amplification of a nucleic acid sequence located near said 3' region of the glucocorticoid receptor gene, Southern Blotting of said 3' region of the glucocorticoid receptor gene and single strand conformational polymorphism (SSCP) mapping of said 3' region of the glucocorticoid receptor gene. The invention also encompasses screening the or a part of the microsatellite region of a glucocorticoid receptor gene for a polymorphism correlated with a polymorphism in or near the 3' region of the gene.

A specific example of the invention described in more detail below, uses one or more primers adapted, following conventional polymerase chain reaction (PCR) techniques, to amplify a nucleic acid sequence located near said 3' region of the glucocorticoid receptor gene In particular within 1000 kb of D5S207, more preferably within 500 kb of D5S207. The product of the PCR includes an amplified nucleic acid sequence. The next step is to determine the size of the amplified sequence. A suitable method is electrophoresis, in which nucleic acids of different sizes migrate in a medium, typically a gel, at a rate according to their size. Two particular PCR primers have a nucleotide sequence selected from the group of nucleotide sequences consisting of SEQ ID NO: 1 and SEQ ID NO: 2, though other primers may be used for this purpose.

SEQ ID NO: 1 is primer Mfd43CA and has the sequence:

5' TTGGAAGCCTTAGGAAGTGC 3'

SEQ ID NO: 2 is primer Mfd43GT and has the sequence:

5' AAGAATTCTAGTTTCAATACCG 3'

These two primers are adapted to amplify a nucleic acid sequence located within said 3' region of the glucocorticoid receptor gene, specifically located in a microsatellite marker referred to as D5S207. A risk genotype incorporates a D5S207 allele of 129 or 135 bp, a non-risk genotype incorporates a D5S207 allele of 131 bp or 133 bp, and the diagnosis of the invention may be carried out in particular on a human. It is further preferred that the diagnosis of the invention is carried out on a female.

The invention also provides use of means to determine genotype of a microsatellite region of a glucocorticoid receptor gene in manufacture of apparatus for diagnosis of predisposition or susceptibility to Syndrome X. In an embodiment of this aspect of the invention, the PCR primers are adapted to amplify a fragment located within a 3' region of said gene, which region consists of or comprises DNA 1000 kb either side of microsatellite D5S207.

The invention in addition provides a method of identifying an individual predisposed or susceptible to Syndrome X, said method comprising determining genotype of a first gene in said individual, wherein genotype of said first gene is correlated with genotype of a microsatellite region of a glucocorticoid receptor gene in -said individual. The genotype of the first gene is correlated with said microsatellite region if a given genotype of the first gene correlates 75% or more with a certain genotype of said microsatellite region, preferably 85% or more and more preferably at least 90%.

The invention further provides a method of identifying an individual predisposed or susceptible to hypertension, said method comprising determining genotype of a first gene in said individual, wherein genotype of said first gene is correlated with genotype of a microsatellite region of a glucocorticoid receptor gene in said individual The invention still further provides a kit for diagnosis of predisposition or susceptibility to Syndrome X comprising one or more primer nucleic acid molecules for determining genotype of a microsatellite region of a glucocorticoid receptor gene and apparatus for correlating glucocorticoid receptor genotype with risk of predisposition or susceptibility to disease.

A preferred kit of the invention comprises PCR primers adapted to distinguish between risk and non-risk genotypes of a microsatellite region of a glucocorticoid receptor gene. Particularly preferred is one comprising primers adapted for amplification of the whole or a fragment of a region 1000 kb on either side of microsatellite D5S207, such as primers SEQ ID NO: i and SEQ ID NO: 2.

In a specific embodiment of the invention, subjects were divided into hypertensive and normotensive categories according to criteria used in previous studies. Individuals classified as hypertensive (HT) had a blood pressure (BP) prior to treatment of >140/90 mmHg and normotensives (NT) had a BP <140/90 mmHg. DNA was extracted from test subjects and genotyping was performed using fluorescently labelled primers which flanked the glucocorticoid receptor gene microsatellite. Results showed a significant difference in genotypes obtained for HT (n=88) and NT(n 123) groups (X=19.2, P=0.0007). A risk genotype of a particular embodiment of this aspect incorporates a D5S207 allele of 129 or 135 bp, and a non-risk genotype incorporates a D5S207 allele of 131 or 133 bp.

According to the present invention, there Is a significant association of the tested microsatellite marker in the Syndrome X disease hypertension. A specific embodiment of the invention is now described in more detail in the following examples.

EXAMPLES

Example 1

Methods

Subject Recruitment

Prior to commencement of this study, ethics was sought and approved by Griffith University's Ethics Committee for Experimentation on Humans and the University of Sydney Human Ethical Review Committee. Ten mL of blood was collected in lithium heparin tubes from each hypertensive and normotensive participating in the study. These unrelated volunteers gave informed consent and were adult Caucasians of British decent living in Australia. Since these subjects are British derived Caucasians, whose ancestors emigrated from a range of locations within the British Isles within the last 160 years, they are unlikely to suffer from local aggregation of genetic traits as has been noted previously for discrete regional populations within the United Kingdom. Individuals were recruited primarily from the Nambour Skin Cancer Trial and also from general practitioners and from media releases to the public. A final number of 88 predisposed hypertensives, with a blood pressure of 140/90 mmHg or greater, were at the time of blood sampling, receiving anti-hypertensive medication and were the offspring of 2 hypertensive parents, and 123 predisposed normotensives, with a blood pressure of less than 140/90 mmHg and who were the offspring of two normotensive parents over the age of 50 years, were collected for the hypertension cross-sectional study.

After completion of a questionnaire detailing their weight and height measurements, these hypertensive and normotensives along with other normotensives whose parental blood pressure status was unknown, were subdivided into lean and obese categories dependent on their body mass index (BMI), as described previously (Caterson, I. D. Obesity, part of the metabolic syndrome. Clin Biochem Revs 1997; 18: 11–21; Zee R Y L, Schrader A P, Robinson B G, Griffiths L R, Morris B J. Association of HincII RFLP of low density lipoprotein receptor gene with obesity in essential hypertensives. Clin Genet 1995; 47:118–121). One hundred and fifty lean individuals with a BMI less than 26 kg/m² and 94 obese individuals with a BMI of 26 kg/m² were obtained. Individuals were excluded from the study if they had a family history of thyroid disease or diabetes.

Amplification

DNA was extracted using previously published methods (Miller S A, Dykes D D, Polesky H F. A simple salting out procedure for extracting DNA from human nucleated cells. Nuc Acid Res 1988; 16, 1215) and genotyping was performed using fluorescently labelled primers (Weber et al) which flanked D5S207. After a 94° C. denaturing period of 4 min, 35 PCR cycles of 94° C. for 40 s, 60° C. for 90 s followed by 72° C. for 120 s were performed. PCR products representing the 5 alleles of the polymorphism, were detected by capillary electrophoresis on an Applied Biosystems 310 DNA sequencer with GENESCAN™ software. Chi-squared and clump analysis using Monte Carlo simulations (Sham P C, Curtis D. Monte Carlo tests for associations between disease and alleles at highly polymorphic loci. Ann Hum Genet 1995; 59: 97–105) were both used to analyze results. A Monte Carlo approach was used to overcomrie statistical analysis difficulties associated with rare alleles from multi-allelic microsatellite variants.

Results

Effect of D5S207 on Hypertension

Following PCR amplification of the microsatellite variant, D5S207, Genescan analysis was used to identify five alleles ranging in size from 129 bp to 137 bp. The results of the study on 88 hypertensives with a mean age of 54.11±12 years, and 123 predisposed normotensives with a mean age of 48.34±12.8 years, are shown in Table 1. As indicated, allele frequencies for four of the alleles varied in the tested hypertensive and normotensive populations with a lower frequency seen for the 131 and 133 bp alleles in hypertensives. All tested populations were shown to be in Hardy-Weinberg equilibrium. Statistical chi-squared analysis of glucocorticoid receptor genotypes (Table 1) illustrated a significant association of the glucocorticoid receptor with hypertension ($\chi^2$=19.13, P=0.0007). Furthermore, Clump analysis with Monte Carlo simulations also resulted in a significant difference ($\chi^2$=8.3, P=0.017) when 5000 simulations were performed.

In this association study a microsatellite marker, D5S207, was used to genotype 88 hypertensives and 123 normotensive individuals to determine whether an area in the vicinity of the 3' end of the glucocorticoid receptor is involved in hypertension development.

The results of this study indicate that there is an association of D5S207 variants with hypertension ($\chi^2$=19.2, P=0.0007; Monte Carlo $\chi^2$=8.3, P=0.017, n=5000) in the tested population The tested microsatellite marker has been co-localised to a 200 kb YAC containing the glucocorticoid receptor gene. This YAC is included in a YAC contig containing the following order of genes, centromere-ILS-FGFA-5'GRL3'-D5S207-D5S210-D5S376-CSF1R-SPARC-D5S119-D5S209 FGfR4-telomere, with the D5S207 located to the 3' side of the glucocorticoid receptor gene, and linkage studies have also confirmed that the microsatellite is located at the 3' end of the glucocorticoid receptor gene with the maximum lod score showing a distance of 1 cM or less (Jabs E W, Li X, Lovett M, Yamaoka L H, Taylor E, Speer M C, Coss C, Cadle R, Hall B, Brown K, Kidd K K, Dolganov G, Polymeropoulos M H, Meyers D A. Genetic and Physical Mapping of the Treacher Collins Syndrome Locus with Respect to Loci in the Chromosome 5q3 Region Genomics 1993; 18: 7–13).

From this study, it appears that polymorphisms in this area of the gene, which contains the ligand binding domain of the glucocorticoid receptor, are correlated with the Syndrome X disease essential hypertension. The invention thus enables diagnosis and treatment before development of disease.

TABLE 1

Comparison of D5S207 alleles in tested predisposed hypertensive and normotensive populations.

| | n | Allele Frequency | | | | | Total Alleles | | | | |
|---|---|---|---|---|---|---|---|---|---|---|---|
| | | 129 | 131 | 133 | 135 | 137 | 129 | 131 | 133 | 135 | 137 |
| Hypertensives | 88 | 0.11 | 0.12 | 0.43 | 0.32 | 0.02 | 20 | 21 | 75 | 57 | 3 |
| Normotensives | 123 | 0.04 | 0.19 | 0.55 | 0.20 | 0.02 | 10 | 46 | 135 | 51 | 4 |

$X^2 = 19.2$,
$P = 0.0007$

What is claimed is:

1. A method of diagnosis of hypertension in a human, said method comprising determining the genotype of the D5S207 microsatellite region of a glucocorticoid receptor gene in said human, identifying whether said genotype is a risk genotype and, if a risk genotype is so identified, then diagnosing said human as hypertensive.

2. A method of identifying a human predisposed or susceptible to hypertension, said method comprising determining the genotype of the D5S207 microsatellite region of a glucocorticoid receptor gene in said human, identifying whether said genotype is a risk genotype and, if a risk genotype is so identified, then diagnosing said human as susceptible or predisposed to hypertension.

3. The method of claim 1 or claim 2 comprising determining whether the human is homozygous or heterozygous for polymorphisms of said D5S207 microsatellite region of the glucocorticoid receptor gene.

4. The method of claim 1 or claim 2, wherein said determination of the genotype of said region is accomplished by screening said region to identify a risk polymorphism in said region, said risk polymorphism being indicative of risk of hypertension or of predisposition or susceptibility to hypertension.

5. The method of claim 4, wherein said screening is accomplished by a technique selected from the group of techniques consisting of amplification of a nucleic acid sequence located within said region, Southern Blotting of said region and single strand conformational polymorphism (SSCP) mapping of said region.

6. The method of claim 2, wherein said determining is accomplished by amplification of a nucleic acid sequence located within said microsatellite region of the glucocorticold receptor gene.

7. The method of claim 6, wherein said amplification is accomplished by the polymerase chain reaction using one or more primers adapted to amplify a nucleic acid sequence located within said microsatellite region of the glucocorticoid receptor gene.

8. The method of claim 7, wherein said primers have a nucleotide sequence selected from the group of nucleotide sequences consisting of SEQ ID NO: 1 and SEQ ID NO: 2.

9. The method of claim 1 or claim 2, wherein said human is a female.

10. A method of diagnosis and treatment of a human susceptible or predisposed to hypertension, comprising determining the genotype of the D5S207 microsatellite region of a glucocorticoid receptor gene in said human, identifying whether said genotype is a risk genotype and, if a risk genotype is so identified, then diagnosing said human as susceptible or predisposed to hypertension, and administering treatment to reduce or delay or prevent hypertension.

11. The method of claim 10 wherein said treatment is selected from the group consisting of administration of an effective amount of antihypertensive pharmaceutical, administration of an effective anti-hypertension therapy or administration of both an effective anti-hypertension therapy and an effective amount of antihypertensive pharmaceutical.

12. The method of claim 10, wherein said risk genotype is a D5S207 allele of length 129 or 135 bp.

13. A method of diagnosing hypertension or susceptibility to hypertension, said method comprising determining the genotype of microsatellite D5S207, identifying whether said genotype is a risk genotype and, if a risk genotype is so identified, then diagnosing said human as hypertensive or susceptible to hypertension, wherein an allele of 129 or 135 bp indicates a risk of hypertension or of susceptibility to hypertension and wherein an allele of 131 or 133 bp indicates the absence of risk of hypertension or of susceptibility to hypertension.

14. The method of claim 4, wherein the risk genotype of said D5S207 microsatellite region includes an allele of 129 or 135 bp.

15. The method of claim 4, wherein the non-risk genotype of said D5S207 microsatellite region includes an allele of 131 or 133 bp.

* * * * *